United States Patent [19]

Lerch et al.

[11] 4,078,081
[45] Mar. 7, 1978

[54] CYCLOPENTANE DERIVATIVES MANUFACTURE

[75] Inventors: Ulrich Lerch, Hofheim, Taunus; Milos Babej, Frankfurt am Main; Wilhelm Bartmann, Neuenhain, Taunus; Rudolf Kunstmann, Hofheim, Taunus, all of Germany

[73] Assignee: Hoechst Aktiengesellschaft, Frankfurt am Main, Germany

[21] Appl. No.: 582,927

[22] Filed: Jun. 2, 1975

[30] Foreign Application Priority Data

Jun. 4, 1974   Germany .............................. 2426853

[51] Int. Cl.$^2$ .................... C07C 177/00; A61K 31/19; A61K 31/215
[52] U.S. Cl. .............................. 424/305; 260/345.8 R; 260/463; 260/467; 260/514 D; 260/345.8 P; 424/301; 424/304; 424/308; 424/317; 560/53; 560/106; 560/122
[58] Field of Search ..................... 260/468 D, 514 D; 424/305, 317

[56] References Cited
FOREIGN PATENT DOCUMENTS

820,008   3/1975   Belgium .............................. 260/468

*Primary Examiner*—Robert Gerstl
*Attorney, Agent, or Firm*—Curtis, Morris & Safford

[57] ABSTRACT

The present invention relates to new cyclopentane derivatives having the formula

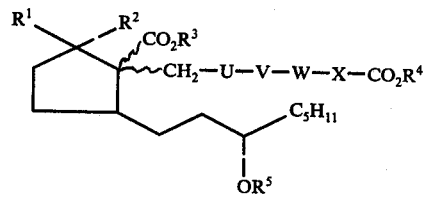

and to a process for their manufacture. The compounds can be used as medicaments due to their antiprostaglandin effect.

9 Claims, No Drawings

CYCLOPENTANE DERIVATIVES MANUFACTURE

The present invention relates to new cyclopentane derivatives and to a process for their manufacture.

Prostaglandins are a group of natural substances which can be isolated from various animal tissues. In mammals they have a great number of pharmacological actions, among which there may be mentioned, for example, the influence on the contraction of the smooth muscles and on the blood pressure. Further pharmacological properties are described, inter alia, in M. F. Cuthbert, "The Prostaglandins", Pharmacological and Therapeutic Advances, William Heinemann Medical Books, Ltd. London 1973.

The present invention relates to cyclopentane derivatives related to the natural prostaglandins and having the formula I

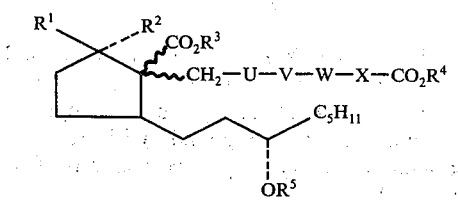

wherein $R^1$ and $R^2$ together denote oxygen or one is a hydrogen atom and the other is a hydroxyl group, $R^3$ is an alkyl group having up to 5 carbon atoms, $R^4$ is a hydrogen atom, an alkyl group having 1 to 10 carbon atoms or a physiologically tolerable mono- or polyvalent cation, $R^5$ is a hydrogen atom, a straight chained or branched, saturated or unsaturated aliphatic hydrocarbon radical or an araliphatic radical, each radical having up to 20 carbon atoms, and wherein a —CH$_2$— group may be replaced by an oxygen or sulfur atom or a carbonyl group or means an alkyl radical having 1 to 5 carbon atoms, which is substituted by a cyano group or by a low-molecular alkoxy-carbonyl group, or stands for a cycloalkyl radical having from 5 to 8 carbon atoms, the —CH$_2$— group in the 2-position of which is replaced by an oxygen or sulfur atom, or an aliphatic, cycloaliphatic, aromatic or araliphatic acyl radical having up to 20 carbon atoms or a low-molecular alkoxy-carbonyl group, U is a (CH$_2$)$_m$—group wherein $m$ is 0 or an integer from 1 to 5, a

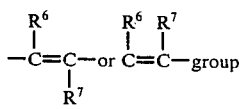

wherein $R^6$ and $R^7$, which are identical or different, each is a hydrogen atom or an alkyl group having up to 5 carbon atoms, , V is a direct bond, an oxygen atom, or a radical of the formula

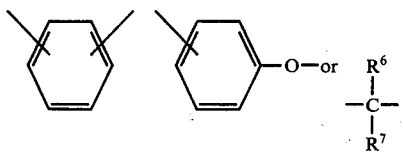

wherein $R^6$ and $R^7$ which are identical or different, each is a hydrogen atom or an alkyl group having up to 5 carbon atoms, W is a direct bond or a radical of the formula

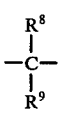

wherein $R^8$ and $R^9$, which are identical or different, each is a hydrogen atom or an alkyl group having up to 5 carbon atoms, X is a (CH$_2$)$_n$—group, wherein $n$ is 0 or an integer from 1 to 5.

The invention also relates to a process for the preparation of cyclopentane derivatives of the formula I, to pharmaceutical preparations containing these compounds as active substances.

The process comprises a. reducing compounds of the formula II

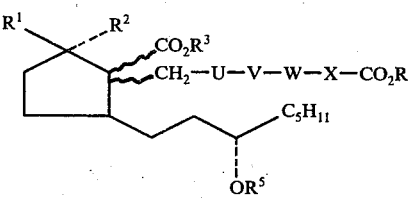

wherein $R^1$, $R^2$, $R^3$, $R^4$ and $R^5$ and U, V, W and X are defined as in formula I, but do not contain any aliphatic carbon-carbon multiple bond, to give compounds of the formula Ia

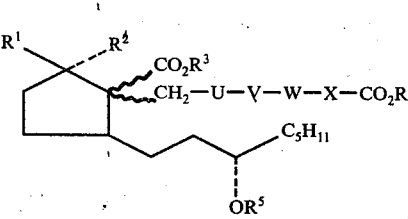

wherein $R^1$ to $R^5$ and U, V, W and X are defined as in formula I, but do not contain any aliphatic carbon-carbon-multiple bond, or b. reducing compounds of the general formula III

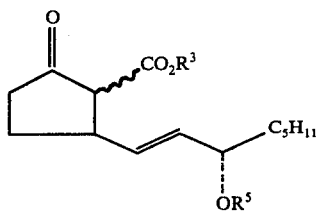

wherein $R^3$, $R^4$ and $R^5$ are defined as in formula I, to compounds of the formula IV

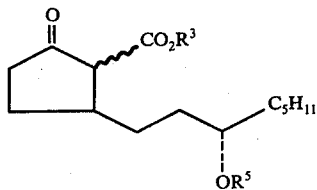

wherein $R^3$, $R^4$ and $R^5$ are defined as in formula I, wherein $R^5$ does not contain any carbon-carbon-multiple bond, and reacting the compounds of the formula IV in an aprotic solvent in the presence of bases with halogenated carboxylic acid esters of the general formula V

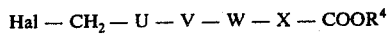

wherein Hal is a halogen atom and U, V, W, X and $R^4$ are defined as in formula I, to give compounds of the formula Ib

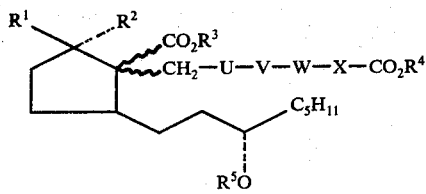

wherein $R^3$, U, V, W and X are defined as in formula I and $R^1$ and $R^2$ each is oxygen, $R^4$ is alkyl having 1 to 10 carbon atoms and $R^5$ is defined as in formula I but does not contain any carbon-carbon-multiple bonds, or, c. solvolizing compounds of the formula Ic

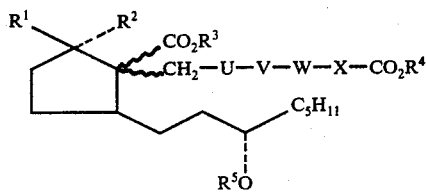

wherein $R^1$, $R^2$, $R^3$, U, V, W and X are defined as in formula I, $R^4$ is alkyl having 1 to 10 carbon atoms and $R^5$ is a cycloalkyl radical having 5 to 8 carbon atoms, wherein the —$CH_2$— group in the 2-position is replaced by an oxygen atom or a sulfur atom, or $R^5$ is an 1-alkoxyalkyl group, in the presence of an acid to compounds of the formula Id

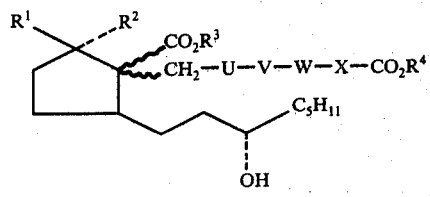

wherein $R^1$, $R^2$, $R^3$, U, V, W and X are defined as in formula I and $R^4$ is alkyl having 1 to 10 carbon atoms, or d. reacting compounds of the formula Ie

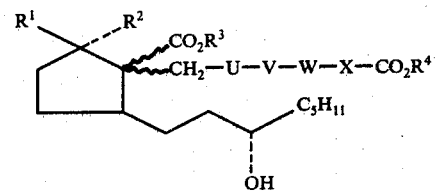

wherein $R^3$, U, V, W and X are defined as in formula I, $R^1$ and $R^2$ together are oxygen and $R^4$ is alkyl having 1 to 10 carbon atoms, with alkylating agents or acylating agents or adding them to compounds with activated carbon-carbon-double bond, to give compounds of the general formula If

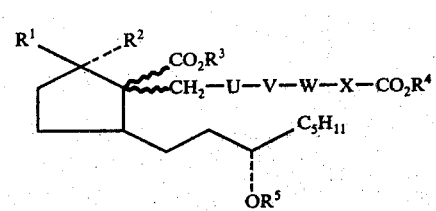

wherein $R^3$, $R^5$, U, V, W and X are defined as in formula I, $R^1$ and $R^2$ together are oxygen and $R^4$ is alkyl having 1 to 10 carbon atoms, or e. reducing compounds of the formula I e or I f to compounds of the formula I g

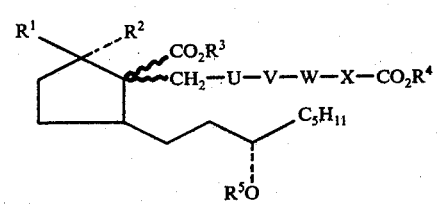

wherein $R^3$, $R^5$, U, V, W and X are defined as in formula I, $R^4$ is alkyl having 1 to 10 carbon atoms and $R^1$ and $R^2$ are different and each is hydrogen or hydroxyl, or f. saponifying compounds of the formula I g partially in an alkaline medium to compounds of the formula I h

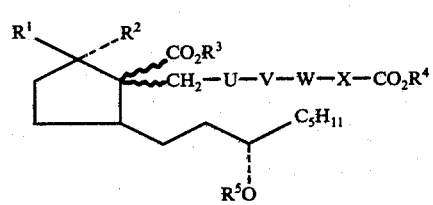

wherein $R^1$, $R^2$, $R^3$, $R^5$, U, V, W and X are defined as in formula I g, $R^4$ is hydrogen or a physiologically tolerable mono- or multivalent cation and $R^5$ is defined as in formula I, but does not mean acyl or alkoxycarbonyl, and converting the salts so obtained, if desired, into the free acids or into ether salts.

The substituent $R^3$ is preferably a methyl or ethyl group. The preferred meanings given for the substituent $R^4$ are hydrogen, $C_1$ - $C_5$-alkyl and alkali metal ions or alkaline-earth metal ions. Moreover, the cations formed from organic bases, such as benzyl amine, morpholine, piperidine or also aminocarboxylic acid esters, such as glutamic acid diethyl ester are considered.

Of the meanings given for $R^5$ are preferred hydrogen, straight chained alkyl radicals having 1 - 8 carbon atoms and araliphatic hydrocarbon radicals having up to 8 carbon atoms in which a —$CH_2$ group may be substituted by an O— or an S—atom or a CO—group, straight chained aliphatic $C_1$ - $C_5$-hydrocarbon radicals having one or more double bonds or a triple bond, alkyl radicals having 1 to 5 carbon atoms which is substituted by a cyano or a $C_2$- $C_4$-alkoxy-carbonyl group, cycloalkyl radicals having 5 to 8 carbon atoms, in which the —$CH_2$—group in 2-position is replaced by an O— or an S—atom, aliphatic, aromatic and araliphatic acyl radicals having up to 8 carbon atoms and alkoxycarbonyl groups having 2 - 4 carbon atoms.

Especially preferred are hydrogen and the tetrahydropyranyl radical.

Especially suitable radicals for $R^5$ are: the methyl, ethyl, propyl, butyl, pentyl, octyl, allyl, propargyl, benzyl methoxymethyl, thiomethoxymethyl, 1-methoxyethyl, acetonyl, 3-oxobutyl, phenacyl, cyanomethyl, cyanoethyl, 2-cyanopropyl, ethoxycarbonylmethyl, methoxycarbonylethyl, acetyl, octanoyl, succinoyl, 2-carboxybenzoyl, methoxycarbonyl, ethoxycarbonyl radical.

U preferably denotes a polymethylene chain having up to 3 $CH_2$—groups. Of the other radicals mentioned for U are preferred those in which $R^6$ or $R^7$ denotes an alkyl radical having up to 3 carbon atoms. The members X, W and V conjointly form preferably an optionally branched chain having up to 10 members. If V denotes a phenylene or phenoxy radical the radicals U and W can be in o-, m- or p-position relative to each other.

The compounds of the invention of the formula I may be stereoisomers with regard to the positions 8 and 12 when $R^1$ and $R^2$ together are an oxygen atom, and they may be stereoisomers with regard to the positions 8, 9 and 12 when $R^1$ and $R^2$ are a hydrogen atom and a hydroxyl group. The compounds of the invention may be prepared and used in the form of their mixtures of isomers, or one or more isomers may be enriched with the aid of usual separating processes, for example, thin layer or column chromatography or may be isolated in pure form and used in this form.

The reduction of a compound of formula II to a compound of formula I a or of a compound of formula III, which may be obtained according to the method described in Belgian Patent Specification No. 766,521; to a compound of formula IV may be effected according to methods known for the introduction of hydrogen at carbon-carbon double bonds, for example catalytic hydrogenation, chemical or microbiological reduction.

For the catalytic hydrogenation there may suitably be used metals, such as, for example cobalt, iridium, rhodium, preferably nickel, palladium and platinum in finely dispersed form, optionally on carriers like calcium sulfate, strontium sulfate or barium sulfate, calcium, strontium, or barium carbonate, aluminum oxide, kieselguhr or active charcoal, moreover catalysts, such as for example nickel boride, nickel or copper chromite, ruthenium oxide or soluble metal complex compounds, such as for example tris-(triphenylphosphine)rhodium chloride, or tris-(triphenylphosphine)-ruthenium dichloride. Furthermore metal salts, such as nickel chloride or cobalt chloride together with complex hydrides, such as $NaBH_4$ or lithium-tertiary-butoxy-aluminum hydride are suitable, as described in Tetr.Lett. 1968, 6313.

The catalytic hydrogenation can be effected, according to the activity of the catalyst, at a temperature ranging from 0° to 150° C, preferably from 20° to 60° C and under hydrogen pressures ranging from 1 to 100 atmospheres, preferably under normal pressure.

Suitable solvents are those which are not reduced under the conditions chosen, such as for example hydrocarbons, for example benzene, ethers, for example diethyl ether, tetrahydrofurane, 1,2-dimethoxyethane and dioxane, alcohols, for example methanol, ethanol, isopropanol and tertiary butanol, esters for example ethyl acetate, carboxylic acids, for example glacial acetic acid, dipolar aprotic solvents, for example dimethyl formamide, N-methylpyrrolidone or hexamethyl phosphoric acid triamide.

In the catalytic hydrogenation of compounds in which $R^5$ is tetrahydropyranyl or 1-alkoxyalkyl, in protic solvents, such as ethanol, this radical is split off in the presence of catalytic amounts of acid and replaced by hydrogen. A chemical reducing agents is, for example diimine (cf. J. org. Chem. 30, 3985 (1965).

The mixture is subsequently worked up in usual manner and the products may be purified by chromatography.

The starting compounds of formula II may be prepared according to the German Offenlegungsschrift No. 2,332,081.

The reaction of a compound of the formula IV with a compound of the formula V occurs according to known methods, preferably at temperatures within the range of room temperature to 140° C and in an inert atmosphere. It is advantageous to carry out the reaction as follows:

A compound of formula IV, in which $R^5$ is preferably the tetrahydropyranyl or a low molecular weight 1-alkoxyalkyl radical, is dissolved in an absolutely dry, aprotic solvent, preferably benzene, toluene or xylene, and from 1 to 1.5 mols of an anhydrous base, preferably sodium ethylate or potassium-tert.-butylate, are added, and the mixture is stirred for a period of from 30 minutes to three hours in an inert gas atmosphere at room temperature.

1 to 2 Mols of a halogenated carboxylic acid ester of the formula V are then added, and the mixture is stirred at a temperature within the range of from 20° C to 140° C, depending on the reactivity of the halogen compound used, for between one and 20 hours, with exclusion of oxygen (see Belgian Patent Specification No. 766,521).

The mixture is subsequently worked up in usual manner. The resulting compounds, which are mostly obtained as oils, may be purified by chromatography.

As halogenated carboxylic acid esters of the formula V there may preferably be used those in which Hal is bromine or iodine. There may be mentioned for example:

7-Iodo-heptanoic acid ethyl ester
7-Iodo-2-methyl heptanoic acid ethyl ester
7-Iodo-3-methyl heptanoic acid ethyl ester
7-Iodo-4-methyl heptanoic acid ethyl ester
7-Iodo-5-methyl heptanoic acid ethyl ester
7-Iodo-6-methyl heptanoic acid ethyl ester
7-Iodo-2-ethyl heptanoic acid ethyl ester
7-Iodo-3-ethyl heptanoic acid ethyl ester
7-Iodo-4-ethyl heptanoic acid ethyl ester
7-Iodo-5-ethyl heptanoic acid ethyl ester
7-Iodo-6-ethyl heptanoic acid ethyl ester
7-Iodo-3-propyl heptanoic acid ethyl ester
7-Iodo-4-propyl heptanoic acid ethyl ester
7-Iodo-5-propyl heptanoic acid ethyl ester
7-Iodo-2-n-butyl heptanoic acid ethyl ester
6-Iodo-hexanoic acid ethyl ester
6-Iodo-2-methyl hexanoic acid ethyl ester
6-Iodo-2-n-butyl hexanoic acid ethyl ester
6-Iodo-2-ethyl hexanoic acid ethyl ester
5-Iodo-pentanoic acid ethyl ester
5-Iodo-2-methyl pentanoic acid ethyl ester
5-Iodo-2-ethyl pentanoic acid ethyl ester
4-Iodo-3-methyl butanoic acid ethyl ester
8-Iodo-octanoic acid ethyl ester
4-Bromo-crotonic acid ethyl ester
4-Bromo-3-methyl crotonic acid methyl ester
7-Iodo-3-oxa-heptanoic acid methyl ester
7-Iodo-3-oxa-heptanoic acid ethyl ester
7-Iodo-3-oxa-heptanoic acid ethyl ester
7-Iodo-2-methyl-3-oxa-heptanoic acid ethyl ester
7-Iodo-3-methyl-4-oxaheptanoic acid ethyl ester
7-Bromo-3-oxa-cis-5-heptenoic acid methyl ester
7-Bromo-3-oxa-trans-5-heptenoic acid methyl ester
6-Iodo-3-oxa-hexanoic acid ethyl ester
5-Iodo-3-oxa-pentanoic acid methyl ester
8-Bromo-4-oxa-cis-6-octenoic acid methyl ester
7-Iodo-5,5-dimethyl-heptanoic acid ethyl ester
7-Iodo-6,6-dimethyl-3-methyl-2,4-heptadienic acid ethyl ester
4-(3-iodopropyl)-benzoic acid ethyl ester
3-(3-iodo-propyl)-benzoic acid ethyl ester
2-(3-iodopropyl)-benzoic acid ethyl ester
2-(4-iodobutyl)-benzoic acid ethyl ester
4-Bromomethyl-hydrocinnamic acid ethyl ester
3-Bromomethyl-hydrocinnamic acid ethyl ester
2-Bromomethyl-hydrocinnamic acid ethyl ester
4-(3-bromomethylphenyl)-butyric acid ethyl ester
4-(2-bromomethylphenyl)-butyric acid ethyl ester
4-(2-iodoethoxy)-benzoic acid ethyl ester
4-(3-iodopropoxy)-benzoic acid ethyl ester
3-(2-iodoethoxy)-benzoic acid ethyl ester
2-(3-iodopropoxy)-benzoic acid ethyl ester
4-Bromomethyl-benzoic acid ethyl ester The esters of the formula I b are oils which can be used directly or after chromatographic purification, for example, on silica gel, or for the further reactions.

According to method (c), a compound of the formula I d is obtained by mildly solvolizing a compound of the formula I c in a suitable solvent, for example a low-molecular weight absolute alcohol, preferably methanol or ethanol, with an acid catalyst, for example an inorganic or organic mono- or polybasic acid or an acid ion exchanger, at a temperature within the range of from 0° to 60° C.

Esters or ethers of the formula I f are prepared according to method (d) in known manner by acylation or alkylation of the free alcohols of the formula I e or their addition to compounds containing activated double bonds. Suitable acylating agents are, for example, organic acidic anhydrides, such as acetic anhydride or organic acid chlorides, for example benzoyl chloride or chloroformiate in the presence of a tertiary base, such as pyridine or triethyl amine. Ethers of the formula I f are prepared in known manner by reacting the alcohol of the formula I e with a corresponding alkylating agent, such as methyl iodide, bromo-acetic acid ethyl ester, chloracetonitrile or chloracetone; ω-bromoacetophenone, allyl bromide or propargyl bromide in an aprotic solvent in the presence of a base, such as for example potassium carbonate.

Ethers of the formula I f can be obtained in known manner by the addition of an alcohol of the formula I e to a compound having activated double bonds, for example cyclic or open-chain vinyl ethers, such as dihydropyrane or ethyl-vinyl ethers or vinyl thioethers in the presence of an acidic catalyst, for example p-toluenesulfonic acid, BF$_3$-etherate or an acidic ion exchanger or to α,β-unsaturated ketones or acid derivatives such as methyl vinyl ketone, acrylic acid methyl ester or acrylo-nitrile in the presence of a basic catalyst, such as, for example potassium tertiary butylate, sodium methylate or a basic ion exchanger.

Compounds of the formula I g are obtained in known manner by reducing a compound of the formula I e or I f with a complex metal hydride, advantageously a metal boranate, preferably alkali metal boranate, such as, for example sodium borohydride or with zinc boronhydride in etheric or alcoholic solution, preferably in an absolute alcoholic solution. Temperatures between −10° and +60° C, generally between 0° and 10° C can be used.

Surprisingly, semiesters of the formula I h may be obtained from the esters of the formula I g if an ester of the formula I g is saponified in a suitable solvent, for example methanol, ethanol, dioxane, tetrahydrofurane or 1,2-dimethoxy-ethane, if desired, in the presence of water with a base, for example sodium, potassium or lithium hydroxide or sodium carbonate.

In this process only the ester group with the radical R$^4$ of the formula I g is converted into the corresponding salt or after a further suitable conversion into the free acid or into another salt.

Examples of compounds which may be prepared according to the process of the invention as illustrated by the Examples are given in the following Table.

(5RS,3″SR)-1-(6′-isobutyloxycarbonyl-3′-methylhexyl)-2-oxo-5-(3″-hydroxy-1″-octyl)-cyclopentanecarboxylic acid methyl ester (5RS,3″SR)-1-(6′-methoxycarbonylhexyl)-2-hydroxy-5-[3″-(2‴-tetrahydropyranyloxy)-1″-octyl]-cyclopentanecarboxylic acid butyl ester (5RS,3″SR)-1-(6′-ethoxycarbonyl-5′-oxa-trans-2′-hexenyl)-2-hydroxy-5-(3″-hydroxy-1″-octyl)-cyclopentanecarboxylic acid ethyl ester (5RS, 3‴SR)-1-[3′-(4″-ethoxycarbonylphenylpropyl]-2-oxo-5-[3‴-(1″″-ethoxyethoxy)-1‴-octyl]-cyclopentanecarboxylic acid ethyl ester (5RS,3″SR)-1-(6′-carboxy-2′-methyl-trans-2-hexenyl)-2-hydroxy-5-(3″-hydroxy-1″-octyl)-cyclopentane carboxylic acid ethyl ester (5RS,3″SR)-1-(6′-ethoxycarbonyl-3′-methylhexyl)-2-oxo-5-(3″-methoxymethoxy-1″-octyl)-cyclopentane carboxylic acid ethyl ester (5RS,3″SR)-1-(6′-octyloxycarbonly-4′-methylhexyl)-2-oxo-5-(3″-propionyloxy-1″-octyl)-cyclopentane carboxylic acid ethyl ester (5RS,3″SR)-1-(6′-methoxycarbonyl-5′,5′-dimethylhexyl)-2-oxo-5-(3″-benzoyloxy-1″-octyl)-cyclopentane carboxylic acid methyl ester (5RS,3‴SR)-1-[3′-(2″-ethoxycarbonylphenoxy)-propyl]-2-oxo-5-(3‴-hydroxy-1‴-octyl)-cyclopentane carboxylic acid ethyl-ester (5RS,3″SR)-1-(6-ethoxycarbonyl-2-cis-hexenyl)-2-oxo-5-(3″-benzyloxy-1″-octyl)-cyclopentane carboxylic acid ethyl ester (5RS,3″SR)-1-(6′-ethoxycarbonyldecyl)-2-oxo-5-(3″-ethoxycarbonylmethoxy-1″-octyl)-cyclopentane carboxylic acid ethyl ester (5RS,3″SR)-1-(6′-ethoxycarbonylhexyl)-2-oxo-5-(3″-allyloxy-1″octyl)-cyclopentane carboxylic acid ethyl ester (5RS,3″SR)-1-(6′-ethoxycarbonyl-3′-methylhexyl)-2-oxo-5-(3″-propargyloxy-1″-octyl)-cyclopentane carboxylic acid ethyl ester (5RS,3″SR)-1-(6′-ethoxycarbonyl-5′-oxahexyl)-2-oxo-5-(3″-methoxy-1″-octyl)-cyclopentane carboxylic acid ethyl ester (5RS,3″SR)-1-(4′-ethoxycarbonylbenzyl)-2-oxo-5-(3″-carboxyethylcarbonyloxy-1″-octyl)-cyclopentane carboxylic acid ethyl ester (5RS,3″SR)-1-(6′-ethoxycarbonylhexyl)-2-hydroxy-5-(3″-heptadecanylcarbonyloxy-1″-octyl)-cyclopentane carboxylic acid ethyl ester (5RS,3″SR)-1-(6-ethoxycarbonylnonyl)-2-oxo-5-(3″-cyanoethoxy-1″-octyl)-cyclopentane carboxylic acid ethyl ester (5RS,3‴SR)-[2″-(ethoxycarbonylethyl)-benzyl]-2-oxo-5-[3‴-(3‴-oxobutoxy)-1‴-octyl]-cyclopentane carboxylic acid ethyl ester (5RS,3″SR)-1-(7′-methoxycarbonylheptyl)-2-hydroxy-5-[3″-(2‴-tetrahydropyranyloxy)-1″-octyl]-cyclopentane carboxylic acid ethyl ester (5RS,3″SR)-1-(5′-ethoxycarbonylhexyl)-2-hydroxy-5-(3″-hydroxy-1″-octyl)-cyclopentane carboxylic acid ethyl ester (5RS,3″SR)-1-(6′-carboxy-5′-oxa-cis-2′-hexenyl)-2-hydroxy-5-(3″-hydroxy-1″-octyl-)-cyclopentane carboxylic acid ethyl ester (5RS,3″SR)-1-(6′-ethoxycarbonylhexyl)-2-oxo-5-(3″-propyloxy-1″-octyl)-cyclopentane carboxylic acid ethyl ester (5RS,3″SR)-1-(6′-ethoxycarbonylhexyl)-2-oxo-5-(3″-octyloxy-1″-octyl)-cyclopentane carboxyl acid ethyl ester (5RS,3″SR)-1-(6′-ethoxycarbonylhexyl)-2-oxo-5-(3″-phenacyloxy-1″-octyl)-cyclopentane carboxylic acid ethyl ester (5RS,3″SR)-1-(6′-ethoxycarbonylhexyl)-2-oxo-5-(3″-cyanmethoxy-1″-octyl)-cyclopentane carboxylic acid ethyl ester (5RS,3″SR)-1-(6′-ethoxycarbonylhexyl)-2-oxo-5-(3″-thiomethoxymethoxy-1″-octyl)-cyclopentane carboxylic acid ethyl ester (5RS,3″SR)-1-(6′-ethoxycarbonylhexyl-2-oxo-5-(3″-ethoxycarbonyloxy-1″-octyl)-cyclopentane carboxylic acid ethyl ester.

It is surprising that the compounds of formula I, which are closely related in structure to the natural prostaglandins, have a strong anti-prostagladin effect. If, for example, a solution of a compound of the invention in water is added to an isolated guinea pig ileum or uterus and if, for example, prostaglandin $E_2$ or $F_2 \alpha$ is added to this preparation, in a concentration which normally stimulates the isolated ileum or the isolated uterus to strong contractions, the spasmogenic effect observed is weaker than that normally produced, and may even be undetectable, depending on the concentrations used.

The compounds of the invention can be used as medicaments due to their anti-prostaglandin effect. It is particularly desirable to inhibit or suppress one or more of the numerous pharmacological effects of the prostaglandins, for example the spasmogenic effect on certain smooth muscles.

The preparations of the invention of the general formula I may be in the form of their aqueous solutions or suspensions or also as solutions in pharmacologically acceptable organic solvents, for example mono- or polyhydric alcohols, dimethylsulfoxide or dimethylformamide, also in the presence of pharmacologically acceptable polymer carriers, for example polyvinyl pyrrolidone. Beside the usual galenic infusion or injection solutions, the preparations may be in the form of tablets, preferably in the form of ointments, emulsions, suppositories or aerosols for local administration.

The preparations of the invention may comprise other pharmacologically active substances, for example prostaglandin synthetase inhibitors, for example, the sodium salt of the acetyl-salicylic acid.

For enteral and parenteral application the daily dose of a compound is from 5 mg to 500 mg, preferably 5 mg to 100 mg. The unit dose form is from 5 to 50 mg of a compound of the invention.

The compounds of the invention are furthermore useful intermediates for the production of prostaglandins.

The following Examples illustrate the invention:

EXAMPLE 1

(5RS,3′SR)-2-oxo-5-[3′-(2″-tetrahydropyranyloxy)-1′-octyl]-cyclopentane carboxylic acid ethyl ester 1.83 g (5 mmols) of (5RS,3′SR)-2-oxo-5-[3′-(2″-tetrahydropyranyloxy)-trans-1′-octenyl]-cyclopentane carboxylic acid ethyl ester were hydrogenated in a corresponding apparatus in 30 ml of absolute ether with 150 mg of 10 % palladium on active charcoal at room temperature. After the consumption of hydrogen was finished (about 2 hours), the catalyst was separated and the solvent was eliminated in vacuo.

The oily residue was pure product that had the same chromatographic characteristics as the starting material. $R_F = 0.30$ (in cyclohexane/ethyl acetate = 8 : 2); 0.51 (benzene/acetone = 9 : 1) (silica gel plates).

In contradistinction to the starting material, the NMRspectrum did not show the multiplet for the olefinic protons at 5.4 – 5.75 ppm. NMR-signals are to be seen at 4.86 ppm (large singlet); at 4.25 ppm (quadruplet) partially superimposed by a multiplet between 3.2 and 4.2 ppm.

EXAMPLE 2

(5RS,3″SR)-1-(6′-ethoxycarbonyl-3′-methylhexyl)-2-oxo-5-[3″-(2‴-tetrahydropyranyloxy)-1″-octyl]-cyclopentane carboxylic acid ethyl ester 1.83 g (5 mmols) of (5RS,3′SR)-2-oxo-5-[3′-(2″-tetrahydropyranyloxy)-1′-octyl]-cyclopentane carboxylic acid ethyl ester was stirred in 20 ml of dry toluene at room temperature with 675 mg (6 mmols) of potassium tert.butylate for 30 minutes under argon and boiled under reflux for 8 hours after the addition of 3.0 g (10 mmoles) of 7-iodo-5-methyl-heptanoic acid ethyl ester. Analysis by thin-layer chromatography (in cyclohexane/ether = 1 : 1 on $Al_2O_3$-plates) signaled the end of the reaction. The reaction mixture was diluted with 100 ml of benzene, the cold organic phase was washed with water, which contained 3 ml of 2 N $NaH_2PO_4$ solution, dried over magnesium sulfate and the solvent was distilled off in vacuo.

The residue was chromatographed on 120 g of silica gel (Merck) with 1.5 l of a mixture of cyclohexane/ethyl acetate = 9 : 1, and the eluate was divided into 90 equal fractions. After evaporating the solvent, fractions 43 - 69 yielded 1.51 g of (5RS,3"SR)-1-(6'-ethoxycarbonyl-3'-methyl-hexyl)-2-oxo-5-[3"(2'"-tetrahydropyranyloxy)-1"-octyl]-cyclo-pentane carboxylic acid ethyl ester.

$R_F$ = 0.26 (in cyclohexane/ethyl acetate = 85 : 15 on $SiO_2$ - plates)

NMR spectrum: 4.62 ppm (1H, large singlet); 3.2 – 4.2 ppm (multiplet, partially superimposed by a quadruplet at 4.15 ppm (4H)

EXAMPLE 3

(5RS,3"SR)-1-6'-ethoxycarbonyl-4'-ethylhexyl)-2-oxo-5-[3"-(2'"-tetrahydropyranyloxy)-1"-octyl]-cyclopentane carboxylic acid ethyl ester 450 mg of (5RS,3"SR)-1-(6'-ethoxycarbonyl-4-ethyl hexyl)-2-oxo-5-[3"-(2'"-tetrahydropyranyloxy)-trans-1"-octenyl]-cyclopentane carboxylic acid ethyl ester in 7 ml of dry THF were hydrogenated with 150 mg of platinum black under normal conditions until hydrogen was no longer consumed. The catalyst and the solvent were removed and the residue was chromatographed on 20 g of silica gel in cyclohexane/ethyl acetate = 9 : 1.

$R_F$ = 0.26 (in cyclohexane/ethyl acetate = 85 : 15)

The NMR was approximately identical with that relating to the product in Example 2.

EXAMPLE 4

(5RS,3"SR)-1-(6'-ethoxycarbonyl-3'-methylhexyl)-2-oxo-5-(3"-hydroxy-1"-octyl)-cyclopentane carboxylic acid ethyl ester a. 2.4 g of (5RS,3"SR)-1-(6'-ethoxycarbonyl-3'-methylhexyl)-2-oxo-5-[3"-(2'"-tetrahydropyranyloxy)-1"-octyl]-cyclopentane carboxylic acid ethyl ester and 150 mg of p-toluenesulfonic acid were stirred under argon at 40° C in 160 ml of absolute ethanol.

After 4 – 5 hours the reaction had come to an end. The reaction solution was adjusted to pH 7 – 8 with triethyl amine, the solvent was removed in vacuo, the residue was taken up in ether, washed with water and dried. Chromatography on 130 g of silica gel in 2.1 l of cyclohexane/ethyl acetate = 8 : 2 yielded 108 fractions. The product (1.4 g) was isolated in vacuo by evaporating fractions 52 – 99.

$R_F$ = 0.29 (in cyclohexane/ethyl acetate/glacial acetic acid = 60 : 40 : 1).

The NMR spectrum did not show the signal at about 4.65 ppm characterizing the tetrahydropyranyl ether grouping.

b. (5RS,3"SR)-1-(6'-ethoxycarbonyl-3'-methylhexyl)-2-oxo-5-(3"-hydroxy-1"-octyl)-cyclopentane carboxylic acid ethyl ester 650 mg of (5RS,3"SR)-1-(6'-ethoxycarbonyl)-3'-methylhexyl)-2-oxo-5-[3"-(2'"-tetrahydropyranyloxy)-trans-1"-octenyl]-cyclopentane carboxylic acid ethyl ester were hydrogenated in the presence of 20 mg of p-toluenesulfonic acid in 10 ml of ethanol with 150 mg of 10% palladium on carbon. Hydrogenation was finished after 30 – 40 hours. After separating the catalyst the solvent was evaporated in vacuo and the oily residue was chromatographed on silica gel as described in Example 4.

EXAMPLE 5

(5RS,3"SR)-1-(6'-ethoxycarbonyl-3'-methylhexyl)-2-hydroxy-5-[3"-(2'"-tetrahydropyranyloxy)-1"-octyl]-cyclopentanecarboxylic acid ethyl ester To 538 mg (1 mmol) of (5RS,3"SR)-1-(6'-ethoxycarbonyl-3'-methyl-hexyl)-2-oxo-5-[3"-(2'"-tetrahydropyranyloxy)-1"-octyl]cyclopentanecarboxylic acid ethyl ester in 15 ml of absolute ethanol were added portionwise 115 mg (3mmols) of sodium boron hydride.

The mixture was stirred for 2 hours under argon, adjusted to pH 7 with glacial acetic acid at 0° C and the solvent was removed in vacuo at a bath temperature of 20° C. The residue was washed with ether and water, the organic phase was dried with $MgSO_4$ and evaporated. The remaining oil was chromatographed on 15 g of silica gel with cyclohexane/ethyl acetate (85 : 15).

$R_F$ = 0.39 (in cyclohexane/ethyl acatate = 7 : 3).

The NMR spectra of the two isomers are approximately identical. 4.63 ppm (large signal); 3.2 – 4.3 ppm (quadruplet, superimposed by a multiplet).

EXAMPLE 6

(5RS,3"-SR)-1-(6'-ethoxycarbonyl-3'-methylhexyl)-2-hydroxy-5-(3"-hydroxy-1"-octyl)-cyclopentanecarboxylic acid ethyl ester 300 mg of (5RS,3"-SR)-1-(6'-ethoxycarbonyl-3'-methyl-hexyl)-2-hydroxy-5-[3"-(2'"-tetrahydropyranyloxy)-1"-octyl]-cyclopentanecarboxylic acid ethyl ester were treated as in Example 4 *a* with p-toluenesulfonic acid in ethanol and worked up in an analogous manner.

Upon chromatography on 15 g of silica gel, a colorless oil was obtained which had an $R_F$-value of 0.49 (in cyclohexane/ethyl acetate/glacial acetic acid = 40 : 60 : 1).

EXAMPLE 7

(5RS,3"SR)-1-(6'-carboxy-3'-methylhexyl)-2-hydroxy-5-[3"-(2'"-tetrahydropyranyloxy)-1"-octyl]-cyclopentanecarboxylic acid ethyl ester 420 mg of (5 RS,3"SR)-1-(6'-ethoxycarbonyl-3'-methyl-hexyl)-2-hydroxy-5-[3"-(2'"-tetrahydropyranyloxy)-1"-octyl]-cyclopentane-carboxylic acid ethyl ester were stirred at room temperature for 15 hours under argon with 7 ml of 0.6 N NaOH and 10 ml of methanol, the solvent was removed at a bath temperature of 25° C in vacuo and the oily residue was adjusted to pH 2 after the addition of ether and water with dilute HCl shile thoroughly cooling.

The organic phase was washed until free from acid, dried and evaporated.

The crude product was chromatographed on 40 g of silica gel with cyclohexane/acetone = 7 : 3.

$R_F$ = 0.39 (in cyclohexane/acetone = 1 : 1)

NMR-spectrum: 4.66 ppm (1H); 3.3 - 4.5 ppm (5H)

EXAMPLE 8

(5RS,3″SR)-1-(6′-carboxy-3′-methylhexyl)-2-hydroxy-5-(3″-hydroxy-1″-octyl)-cyclopentanecarboxylic acid ethyl ester a. 450 mg of (5RS, 3″-SR)-1-(6′-carboxy-3′-methylhexyl)-2-hydroxy-5-[3″-(2‴-tetrahydropyranyloxy)-1″-octyl]-cyclopentanecarboxylic acid ethyl ester were heated for 90 minutes at 70° C under argon in 10 ml of ethanol and 4 ml of 2% aqueous oxalic acid. The reaction solution was concentrated under reduced pressure and the residue was dissolved in ether and saturated sodium chloride solution. The organic phase was evaporated in vacuo after drying and the oil obtained was chromatographed on 40 g of SiO₂ with cyclohexane/ethyl acetate/glacial acetic acid = 50 : 50 : 1.

$R_F$ = 0.24 (cyclohexane/ethyl acetate/glacial acetic acid = 40 : 60 : 1).

NMR-spectrum: 4.9 ppm (3 hydroxyl protons, large singlet); 3.8 - 4.3 ppm (4H, multiplet)

b. 300 mg of (5RS,3″SR)-1-(6′-ethoxycarbonyl-3′-methylhexyl)-2-hydroxy-5-(3″-hydroxy-1″-octyl)-cyclopentanecarboxylic acid ethyl ester, 5 ml of 0.6 N NaOH and 7 ml of methanol were stirred for 24 hours at room temperature under argon. After concentration in vacuo, saturated sodium chloride solution was added and the mixture was adjusted to pH 1 - 2 with 2 N HCl The product was taken up in ether and purified as described in Example 8 a.

EXAMPLE 9

(5RS,3″SR)-1-(6′-ethoxycarbonyl-5′-methylhexyl)-2-oxo-5-[3″-(2‴-tetrahydropyranyloxy)-1″-octyl]-cyclopentanecarboxylic acid ethyl ester The above Example was carried out in analogy to Example 2 with the use of (5RS,3′SR)-2-oxo-5-[3′-(2″-tetrahydropyranyloxy)-1′-octyl]-cyclopentanecarboxylic acid ethyl ester and 7-iodo-3-methylheptanoic acid methyl ester.

$R_F$ = 0.55 (on silica gel, in cyclohexane/ethyl acetate = 6 : 4)

NMR-spectrum: approximately identical with the NMR-spectrum referring to the product obtained according to Example 2.

EXAMPLE 10

(5RS,3″SR)-1-(6′-ethoxycarbonyl-cis-2′-hexenyl)-2-oxo-5-[3″-(2‴-tetrahydropyranyloxy)1″-octyl]-cyclopentanecarboxylic acid ethyl ester The above Example was carried out in analogy to Example 2 with the use of (5RS,3′SR)-2-oxo-5-[3′-(2″-tetrahydroxypyranyloxy)-1′-octyl]-cyclopentanecarboxylic acid ethyl ester and 7-iodo-cis-5-heptenoic acid ethyl ester.

$R_F$ = 0.25 (cyclohexane/ethyl acetate = 85 : 15)

NMR-spectrum: 5.5 - 5.8 ppm (2 H, multiplet)

EXAMPLE 11

(5RS,3″SR)-1-(6′-ethoxycarbonyl-5′-oxahexyl)-2-oxo-5-[3″-(2‴-tetrahydropyranyloxy)-1″-octyl]-cyclopentanecarboxylic acid ethyl ester The above Example was carried out in analogy to Example 2 with the use of (5RS,3′SR)-2-oxo-5-[3′-(2″-tetrahydropyranyloxy)-1′-octyl]-cyclopentanecarboxylic acid ethyl ester and 7-iodo-3-oxaheptanoic acid ethyl ester $R_F$ = 0.37 (in cyclohexane/ethyl acetate = 7 : 3)

NMR-spectrum: 3.2 - 4.7 ppm (12 H)

EXAMPLE 12

(5RS,3″SR)-1-(6′-methoxycarbonyl-5′-oxa-cis-2′-hexenyl)-2-oxo-5-[3″-(2‴-tetrahydropyranyloxy)-1″-octyl]-cyclopentanecarboxylic acid ethyl ester The above example was carried out in analogy to Example 2 with the use of (5RS,3′SR)-2-oxo-5-[3′-(2‴-tetrahydropyranyloxy)-1′-octyl]-cyclopentanecarboxylic acid ethyl ester and 7-bromo-3-oxa-cis-5-heptenoic acid ethyl ester.

$R_F$ = 0.33 ( in cyclohexane/ethyl acetate = 8 : 2)

NMR-specturm: 5.5 - 5.8 ppm (2 olefinic H); 4.65 ppm (1H)

EXAMPLE 13

(5Rs,3‴-SR)-1-[3′-(4″-ethoxycarbonylphenyl)-propyl]-2-oxo-5-[3‴-(2″″-tetrahydropyranyloxy)-1‴-octyl]-cyclopentanecarboxylic acid ethyl ester.

The Example was carried out in analogy to Example 2 with the use of (5RS,3′SR)-2-oxo-5-[3′-(2″-tetrahydropyranyloxy-1′-octyl]-cyclopentanecarboxylic acid ethyl ester and 4-(3-iodopropyl)-benzoic acid ethyl ester.

$R_F$ = 0.60 (in cyclohexane/ethyl acetate = 1 : 1)

NMR-spectrum: 7.6 ppm (4H, A₂B₂); 4.65 ppm (1H); 4.55 - 3.3 ppm (7 H).

EXAMPLE 14

(5RS,3‴SR)-1-[3′-(2″-ethoxycarbonylphenoxy)-propyl]-2-oxo-5-[3‴-(2″″-tetrahydropyranyloxy)-1‴-octyl]-cyclopentanecarboxylic acid ethyl ester The above Example was carried out in analogy with Example 2 with the use of (5RS,3′SR)-2-oxo-5[3′-(2″-tetrahydropyranyloxy)-1′-octyl]-cyclopentanecarboxylic acid ethyl ester and 2-(3-iodopropoxy-)-benzoic acid ethyl ester.

$R_F$ = 0.39 (cyclohexane/ethyl acetate = 7 : 3)

NMR-spectrum: 6.8 - 7.9 ppm (4 H, multiplet); 4.65 ppm (1H, large singlet); 3.2 - 4.6 ppm (9 H, multiplet)

EXAMPLE 15

(5RS,3″SR)-1-(6′-ethoxycarbonyl-4′-ethylhexyl)-2-oxo-5-(3″-hydroxy-1″-octyl)-cyclopentanecarboxylic acid ethyl ester The above compound was prepared in analogy to Example 4 a from (5RS,3″SR)-1-(6′-ethoxycarbonyl-4′-ethylhexyl)-2-oxo-5-[3″-(2‴-tetrahydropyranyloxy)-1″-octyl]-cyclopentanecarboxylic acid ethyl ester.

(Example 3)

$R_F$ = 0.35 (cyclohexane/ethyl acetate/glacial acetic acid; = 60 : 40 : 1

NMR-spectrum: 4.18 ppm (quadruplet, 4H); 3.60 ppm (large multiplet, 1H)

EXAMPLE 16

(5RS,3''SR)-1-(6'-ethoxycarbonyl-3'-ethylhexyl)-2-oxo-5-[3''-(2'''-tetrahydropyranyloxy)-1''-octyl]-cyclopentanecarboxylic acid ethyl ester The above compound was prepared in analogy to Example 2 from (5RS,3'SR)-2-oxo-5-[3'-(2''-tetrahydropyranyloxy)-1'-octyl]-cyclopentanecarboxylic acid ethyl ester and 7-iodo-5-ethylheptanoic acid ethyl ester.

$R_F$ = 0.33 ($CHCl_3$)

NMR-spectrum: 4.6 ppm (large signal, 1H); quadruplet at 4.15 ppm (4H), partially superimposed by a multiplet.

EXAMPLE 17

(RS,3''SR)-1-(6'-ethoxycarbonyl-3'-ethylhexyl)-2-oxo-5-(3''-hydroxy-1''-octyl)-cyclopentanecarboxylic acid ethyl ester The above compound was prepared in analogy to Example 4a from (5RS,3''SR)-1-(6'-ethoxycarbonyl-3'-ethylhexyl)-2-oxo-5-[3''-2'''-tetrahydropyranyloxy)-1''-octyl]-cyclopentane-carboxylic acid ethyl ester.

$R_F$ = 0.14 ($CHCl_3$)

NMR-spectrum: 3.95 – 4.2 ppm (quadruplet,4H); 3.4 – 3.8 ppm (large multiplet,1H)

EXAMPLE 18

(5RS,3''SR)-1-(6'-ethoxycarbonyl-4'-methylhexyl)-2-oxo-5-[3''-(2'''-tetrahydropyranyloxy)-1''-octyl]-cyclopentanecarboxylic acid ethyl ester The above compound was prepared in analogy to Example 2 from (5RS,3'SR)-2-oxo-5-[3'-(2''-tetrahydropyranyloxy)-1'-octyl]-cyclopentanecarboxylic acid ethyl ester and 7-iodo-4-methylheptanoic acid ethyl ester.

$R_F$ = 0.48 (chloroform/ethyl acetate = 9 : 1)

EXAMPLE 19

(5RS,3''SR)-1-(6'-ethoxycarbonyl-4'-methylhexyl)-2-oxo-5-(3''-hydroxyl-1''-octyl)-cyclopentanecarboxylic acid ethyl ester The above compound was prepared in analogy to Example 4a from (5RS,3''SR)-1-(6'-ethoxycarbonyl-4'-methylhexyl)-2-oxo-5-[3''-(2'''-tetrahydropyranyloxy)-1''-octyl]-cyclopentanecarboxylic acid ethyl ester.

$R_F$ = 0.25 (chloroform/ethyl acetate = 9 : 1)

NMR-spectrum; 0.7 – 1.1 ppm (multiplet, 6H); 3.6 ppm (multiplet, 1H); 4.15 ppm (quadruplet, 4H)

EXAMPLE 20

(5RS,3''SR)-1-(6'-ethoxycarbonyl-2'-methylhexyl)-2-oxo-5-[3''-(2'''-tetrahydropyranyloxy)-1''-octyl]-cyclopentanecarboxylic acid ethyl ester The above compound was prepared in analogy to Example 2 from (5RS,3'SR)-2-oxo-5[3'-(2''-tetrahydropyranyloxy)-1'-octyl]-cyclopentanecarboxylic acid ethyl ester and 7-iodo-6-methylheptanoic acid ethyl ester.

$R_F$ = 0.59 (in cyclohexane/ethyl acetate/glacial acetic acid = 60 : 40 : 1).

EXAMPLE 21

(5RS,3''SR)-1-(6'-ethoxycarbonyl-2'-methylhexyl)-2-oxo-5-(3''-hydroxy-1''-octyl)-cyclopentanecarboxylic acid ethyl ester The above compound was prepared in analogy to Example 4a from (5RS,3''SR)-1-(6'-ethoxycarbonyl-2'-methylhexyl)-2-oxo-5-[3''-(2'''-tetrahydropyranyloxy)-1''-octyl]-cyclopentanecarboxylic acid ethyl ester.

$R_F$ = 0.38 (in cyclohexane/ethyl acetate/glacial acetic acid = 60 : 40 : 1)

NMR-spectrum: 3.9 – 4.2 (quadruplet, 4H); 3.4 – 3.8 (multiplet, 1H).

We claim:
1. A compound of the formula

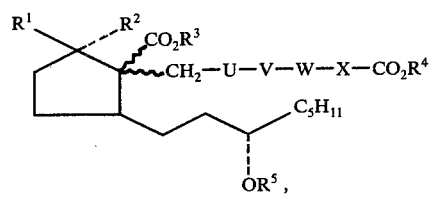

wherein
$R^1$ and $R^2$ together are oxygen, or one is hydrogen and the other is hydroxy;
$R^3$ is alkyl having up to 5 carbon atoms;
$R^4$ is hydrogen, alkyl having 1 to 10 carbon atoms, or is a physiologically tolerable monovalent or polyvalent cation;
$R^5$ is hydrogen, straight-chain or branched, saturated or unsaturated aliphatic or araliphatic hydrocarbon having up to 20 carbon atoms, such an aliphatic or araliphatic hydrocarbon wherein a —$CH_2$— group is replaced by oxygen, sulfur, or carbonyl, or $R^5$ is alkyl having 1 to 5 carbon atoms which is substituted by cyano, alkoxy-carbonyl having 2 to 4 carbon atoms, or $R^5$ is cycloalkyl having 5 to 8 carbon atoms wherein the —$CH_2$— group in the 2-position is replaced by oxygen or sulfur, or $R^5$ is an aliphatic, cycloaliphatic, aromatic, or araliphatic carboxylic acid having up to 20 carbon atoms, or is alkoxy-carbonyl having 2 to 4 carbon atoms;
U is —$(CH_2)_m$—, where $m$ is 0 or an integer from 1 to 5;
V is a direct bond, oxygen, or

wherein P1 $R^6$ and $R^7$ are the same or different and are hydrogen or alkyl having up to 5 carbon atoms;
W is a direct bond or

wherein $R^8$ and $R^9$ are the same or different and are hydrogen or alkyl having up to 5 carbon atoms; and X is $-(CH_2)_n$, where $n$ is 0 or an integer from 1 to 5.

2. A compound as in claim 1, which is (5RS,3″SR)-1-(6′-ethoxycarbonyl-3′-methylhexyl)-2-oxo-5-(3″-hydroxy-1″-octyl)-cyclopentanecarboxylic acid ethyl ester.

3. A compound as in claim 1 which is (5RS,3″SR)-1-(6′-ethoxycarbonyl-3′-methylhexyl)-2-hydroxy-5-(3″-hydroxy-1″-octyl)-cyclopentanecarboxylic acid ethyl ester.

4. A compound as in claim 1 which is (5RS,3″SR)-1-(6′-carboxy-3′-methylhexyl)-2-hydroxy-5-(3″-hydroxy-1″-octyl)-cyclopentanecarboxylic acid ethyl ester.

5. A compound as in claim 1, which is (5RS,3″SR)-1-(6′-ethoxycarbonyl-4′-ethylhexyl)-2-oxo-5-(3″-hydroxy-1″-octyl)-cyclopentanecarboxylic acid ethyl ester.

6. A compound as in claim 1, which is (5RS,3″SR)-1-(6′-ethoxycarbonyl-3′-ethylhexyl)-2-oxo-5-(3″-hydroxy-1″-octyl)-cyclopentanecarboxylic acid ethyl ester.

7. A compound as in claim 1, which is (5RS,3″SR)-1-(6′-ethoxycarbonyl-4′-methylhexyl)-2-oxo-5-(3″-hydroxy-1″-octyl)-cyclopentanecarboxylic acid ethyl ester.

8. A compound as in claim 1, which is (5RS,3″SR)-1-(6′-ethoxycarbonyl-2′-methylhexyl)-2-oxo-5-(3″-hydroxy-1″-octyl)-cyclopentanecarboxylic acid ethyl ester.

9. A pharmaceutical composition having properties antagonistic to numerous prostaglandin properties, said composition comprising a compound as in claim 1, as the active ingredient in combination with a pharmaceutical carrier.

* * * * *